United States Patent [19]

Koturov

[11] Patent Number: 5,269,749
[45] Date of Patent: Dec. 14, 1993

[54] HEAT EXCHANGE DEVICE FOR INDUCING CARDIOPLEGIA

[75] Inventor: Daniel C. Koturov, Lyons, Colo.

[73] Assignee: Cobe Laboratories, Inc., Lakewood, Colo.

[21] Appl. No.: 880,688

[22] Filed: May 8, 1992

[51] Int. Cl.$^5$ ............................................. A61M 1/03
[52] U.S. Cl. ................................. 604/4; 604/113; 165/163
[58] Field of Search .................. 604/4, 27, 48, 113, 604/5, 6; 62/399; 165/163, 156

[56] References Cited

U.S. PATENT DOCUMENTS

| | | | |
|---|---|---|---|
| 3,551,641 | 12/1970 | Truhan | 604/113 X |
| 4,047,526 | 9/1977 | Reynolds et al. | 604/4 |
| 4,257,479 | 3/1981 | Newton | 165/163 X |
| 4,427,009 | 1/1984 | Wells et al. | 604/113 X |
| 4,512,163 | 4/1985 | Wells et al. | |
| 4,529,397 | 7/1985 | Hennemuth et al. | 604/4 |
| 4,568,330 | 2/1986 | Kujawski et al. | 604/4 X |
| 4,653,577 | 3/1987 | Noda | |
| 4,705,508 | 11/1987 | Karnavas et al. | 604/113 |
| 4,787,883 | 11/1988 | Kroyer | 604/113 X |
| 4,878,537 | 11/1989 | Verkaart | 604/113 X |
| 4,883,455 | 11/1989 | Leonard | |
| 5,116,494 | 5/1992 | Chick et al. | 604/4 X |

*Primary Examiner*—Robert A. Hafer
*Assistant Examiner*—Sam Rimell
*Attorney, Agent, or Firm*—Finnegan, Henderson, Farabow, Garrett & Dunner

[57] ABSTRACT

A heat exchange device includes a vessel having a top end and a bottom end, and having a first chamber located in the vessel and a second chamber located in the vessel and separated from the first chamber by a partition. An elongated tube for conveying liquid to be cooled is located in the second chamber and is arranged in a convolution. A port is connected to the first chamber for supplying coolant to that chamber, and a flow path extends between the first and second chambers for permitting fluid flow between the first and second chambers. The flow path is a space between the upper edge of the partition and the top end of the vessel, and the upper edge of the partition uniformly distributes coolant over the elongated tube. A port is located in the second chamber for evacuating coolant from the second chamber.

20 Claims, 2 Drawing Sheets

HEAT EXCHANGE DEVICE FOR INDUCING CARDIOPLEGIA

BACKGROUND OF THE INVENTION

1. Field of the Invention

The invention relates to an heat exchange device for adjusting the temperature of a liquid and, in particular, for cooling blood in order to induce cardioplegia during coronary surgery.

2. Description of the Related Art

The invention is described in connection with the cooling of blood for inducing cardioplegia during coronary surgery. However, it is to be understood that this particular example is given purely by way of illustration and is not intended to limit the scope of the invention as claimed.

During cardiac vascular surgeries and valvular surgeries it is necessary to arrest the pumping activity of the heart. This is usually accomplished by delivering a hypothermic solution of potassium and the patient's blood to the patient in order to cause cardioplegia (heart paralysis). The hypothermic solution can be administered antigrade directly into the coronary ostia or retrograde through the right atrium or the coronary sinus, depending upon surgical need. The hypothermic solution is generally cooled in a heat exchange device which may include a dedicated heater/cooler device or an ice bath.

There are generally two varieties of cardioplegia heat exchange devices that are commercially available. The first variety includes a cooled and/or heated water bath into which a heat exchange element is immersed. In the second variety, a heater/cooler device circulates temperature controlled fluid, such as water around a heat exchange element through which blood passes.

There are a number of drawbacks with the devices currently available. First, a lack of cooling efficiency in some devices can result in too high a myocardial temperature, causing ischemia during the period of cardioplegia administration, which in turn can cause heart tissue damage. Another drawback of related art devices is that temperature may be difficult to precisely control, especially in devices where pockets of coolant can stagnate, leading to differences in coolant temperatures within the device.

A further problem with related art devices is that they tend to be non-compact in size and shape and can be difficult to set up and use.

Finally, some devices have blood flow paths that cause difficulties in eliminating air bubbles and maintaining non-turbulent blood flow. This can be very dangerous because air bubbles released into the patient's circulatory system can cause disastrous results. Further, turbulent blood flow within the cooling device can result in blood trauma and blood cell damage.

SUMMARY OF THE INVENTION

An object of the invention is to provide a heat exchange device that provides high degree of cooling efficiency.

Another object of the invention is to provide a heat exchange device for blood that permits a high degree of temperature control, and reduces the possibility of coolant stagnation within the device.

A further object of the invention is to provide a commercially producible compact heat exchange device that provides a flow path for the liquid to be cooled which eliminates air bubbles and maintains non-turbulent flow.

Additional objects and advantages of the invention will be set forth in part in the description which follows, and in part will be obvious from the description or may be learned by practice of the invention. The objects and advantages of the invention will be realized and attained by means of the elements and combinations particularly pointed out in the appended claims.

To achieve the objects and in accordance with the purposes of the invention, as embodied and broadly described herein, the invention comprises a vessel having a top end and a bottom end, a first chamber located in the vessel, a second chamber located in the vessel and being separated from the first chamber by a partition, elongated tube means located in the second chamber and being arranged in a convolution, the tube means for conveying a liquid to be cooled therein, and means connected to the first chamber for supplying coolant to the first chamber. Flow path means extends between the first and second chambers for permitting fluid flow between the first and second chambers. The flow path means includes means for uniformly distributing coolant over the elongated tube means. Finally, the apparatus of the invention includes means connected to the second chamber for evacuating coolant from the second chamber.

The method of the invention comprises conveying coolant to a first open ended chamber, overflowing the first chamber with coolant so that coolant enters a second chamber, uniformly flowing coolant over a coiled tube surrounding the first chamber, flowing a liquid to be cooled through a coiled tube in the second chamber, and evacuating coolant from the second chamber.

It is to be understood that both the foregoing general description and the following detailed description are exemplary and explanatory only and are not restrictive of the invention, as claimed.

The accompanying drawings, which are incorporated in and constitute a part of the specification illustrate one embodiment of the invention and together with the description, serve to explain the principles of the invention.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

Figure 1:
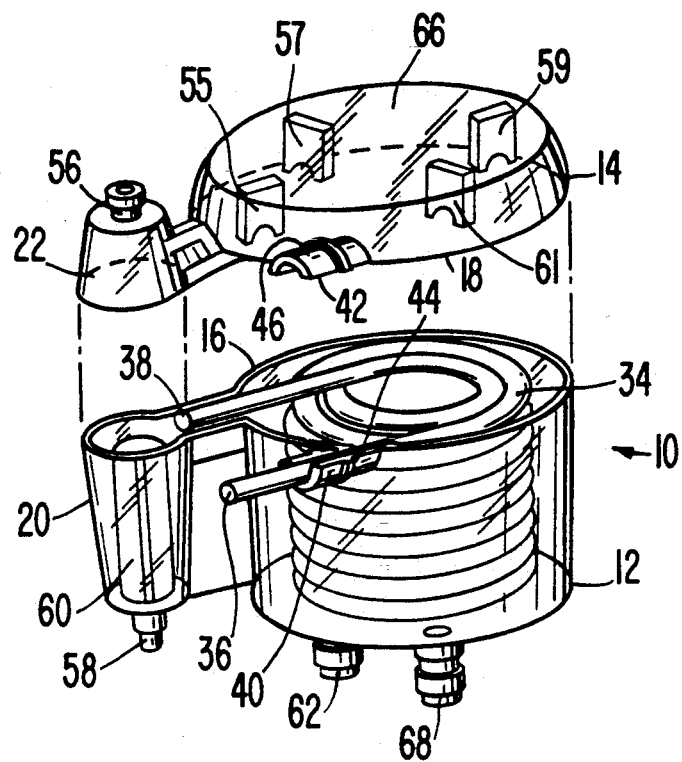
FIG. 1 is a partially exploded view of a heat exchange device in accordance with the present invention.
Figure 2:
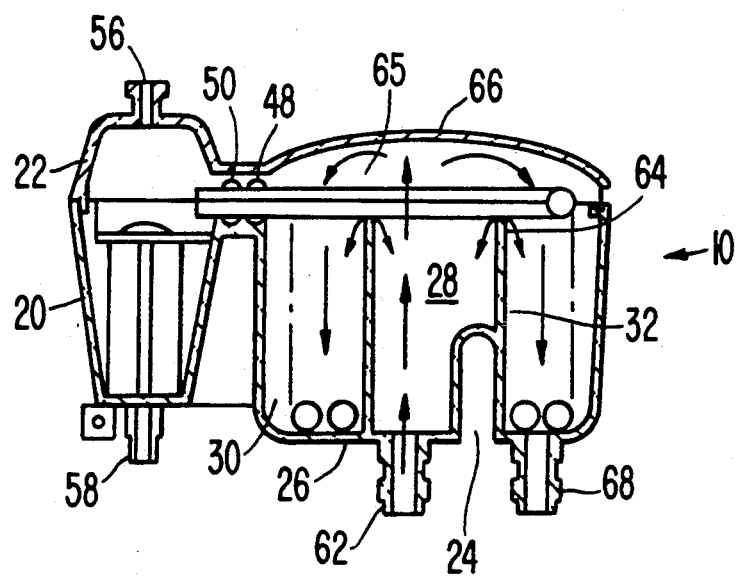
FIG. 2 is a cross-sectional side view of the heat exchange device of FIG. 1.

In accordance with the present invention there is provided a heat exchange device, comprising a vessel having a top end and a bottom end. As embodied herein, and as illustrated in FIGS. 1 and 2, heat exchange device 10 includes receptacle 12 having cap 14 sealed to a top end thereof. A ridge 16 is disposed about the upper edge of receptacle 12, and is filled with an adhesive such as a UV curable glue.

Cap 14 includes a lower edge 18 that fits into ridge 16 of receptacle 12. When cap 14 is disposed on receptacle 12, and the glue in ridge 16 is cured, the glue together with the ridge 16 and edge 18 forms a tight seal between cap 14 and receptacle 12.

It is preferred that both cap 14 and receptacle 12 be manufactured of a transparent material such as polycarbonate. In addition, receptacle 12 may be integrally formed with a bubble trap 20, and cap 14 may be integrally formed with a cap 22 for bubble trap 20. Ridge 16 extends about the upper edge of bubble trap 20, for receiving the lower edge of cap 22, as described previously in connection with cap 14.

Receptacle 12 may also include a socket 24 for receiving a dowel upon which the entire vessel may be selectively mounted to maintain the vessel in a level position during use. Socket 24 is an enclosed cavity that extends through an opening in the bottom end 26 of receptacle 12.

Also in accordance with the invention there is provided a first chamber located in the vessel, and a second chamber located in the vessel and being separated from the first chamber by a partition. As embodied herein, first chamber 28 is located at the center of receptacle 12 and second chamber 30 is provided about the circumference of receptacle 12. A tubular partition 32 is connected to the bottom end 26 of receptacle 12, and divides first chamber 28 from second chamber 30. It is preferable that partition 32 has a tubular shape and is integrally formed with receptacle 12. It is also preferable that the tubular partition 32 have a substantially circular cross-section.

Figure 3:
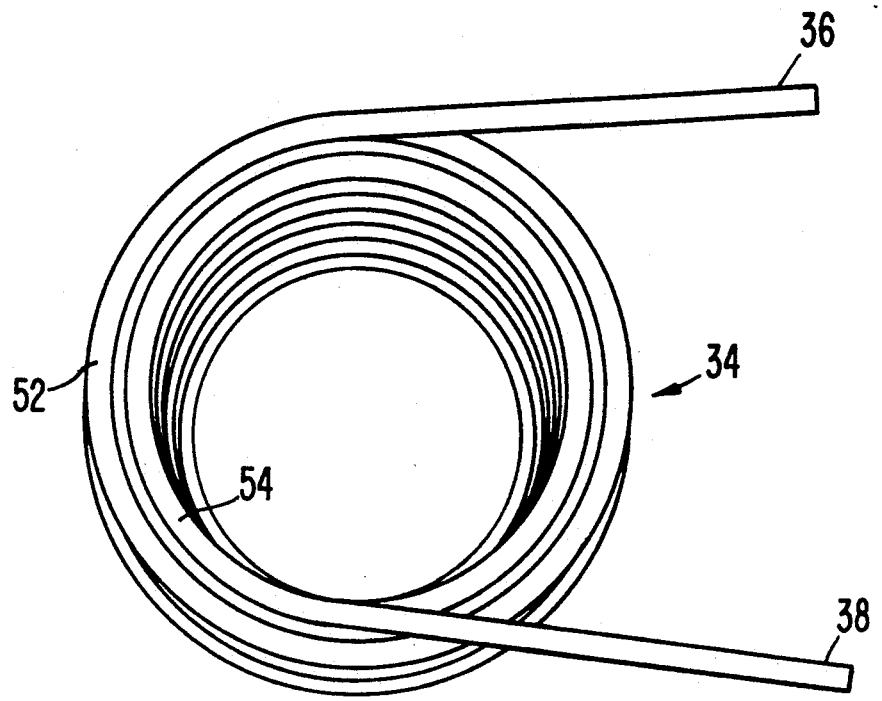
FIG. 3 is a top view of the heat exchange coil illustrated in FIG. 1.
Figure 4:
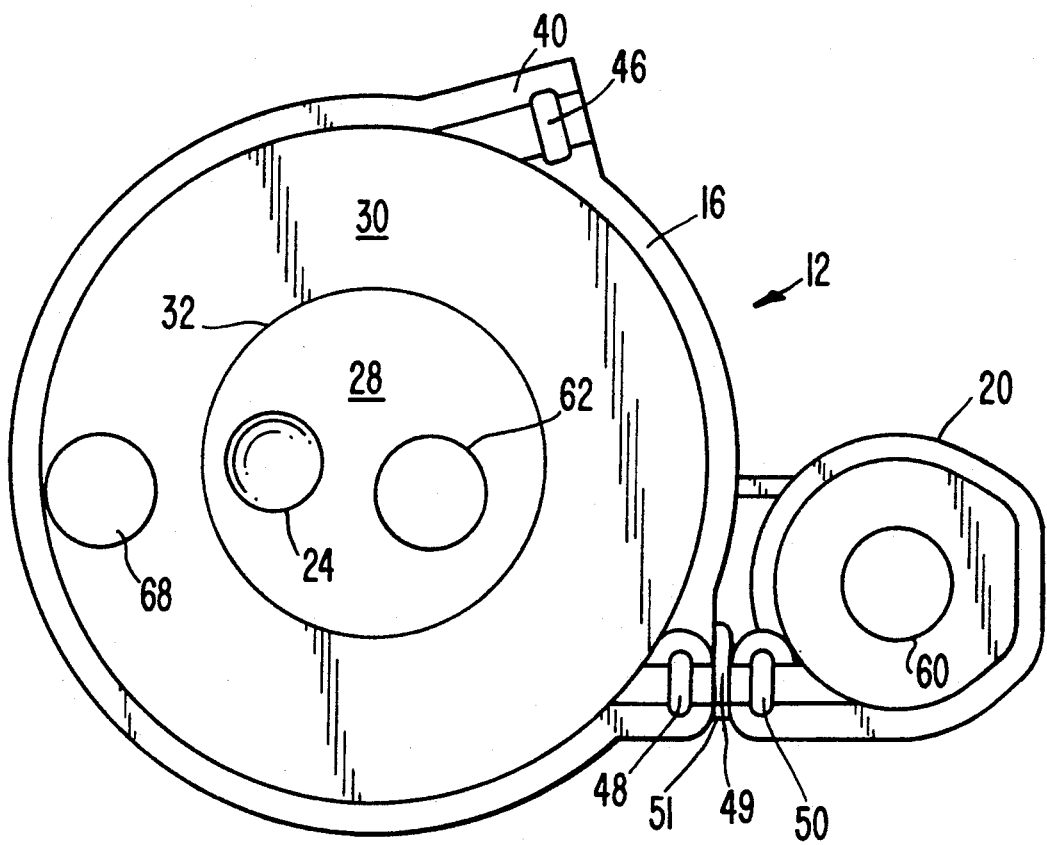
FIG. 4 is a top view of the receptacle illustrated in FIG. 1.

In accordance with the invention there is provided elongated tube means located in the second chamber and being arranged in a convolution, the tube means for conveying a liquid to be cooled therein. As embodied herein, elongated tube means includes stainless steel tube 34 arranged in a convolution about partition 32. It is preferred that stainless steel tube 34 be arranged in a double coiled helix as illustrated in FIG. 3. The double-coiled helix permits a relatively large length of tubing to be housed within a relatively small receptacle. For example, it has been found that the invention works well with an approximately 80 inch long piece of ¼ inch tubing coiled within a vessel having a diameter of approximately 3½ inches and a height of approximately 2¼ inches. In this example, the tubing has a volume of approximately 66 cc while the volume of the vessel is about 300 cc.

Tube 34 includes an inlet end 36 and an outlet end 38. Inlet end 36 passes between flanges 40 and 42 that respectively extend from receptacle 20 and cap 14. Flanges 40 and 42 cooperate to surround a portion of tube 34, and have ridges 44 and 46 that together form a O-ring space about tube 34. When cap 14 is sealed to receptacle 12, the O-ring space formed between flanges 40 and 42 is filled with glue, thereby sealing tube 34 to the flanges 40 and 42, and preventing leakage therebetween.

Similarly, the outlet end 38 of tube 34 extends between an edge region of receptacle 12 and cap 14 that connects receptacle 12 to bubble trap 20. The opening in outlet end 38 communicates with the interior of bubble trap 20. A pair of ridges 48 and 50 are located adjacent each other on receptacle 12 and bubble trap 20, respectively. The regions surrounding ridges 48 and 50 are disconnected from each other except for a single rib 51 extending therebetween. This structure defines a void 49 disposed between ridges 48 and 50. Ridges 48 and 50 are each similar in structure to ridge 46 and each cooperate with corresponding ridges on caps 14 and 22 to form a pair of O-ring seals. This pair of seals prevents leakage about the outlet end 38 of tube 34 and between heat exchange device 10 and bubble trap 20. The double seal and the void 49 are provided o the outlet end 38 of tube 34 as an added measure of security against contamination of the liquid to be cooled in bubble trap 20 by coolant from receptacle 12. In the unlikely event of a failure of the seal corresponding to ridge 48, coolant will spill through void 49 keeping coolant away from bubble trap 20.

In a preferred use, the heat exchange device of the present invention is used to cool a hypothermic solution of blood and anticoagulant. The hypothermic solution enters tube 34 through inlet end 36 located proximate the top of heat exchange device 10. The solution then travels in a first coiled helix 52 from a position beneath the cap 14 to the bottom end 26 of receptacle 12. Subsequently, the solution travels in a second coiled helix 54 within the first coiled helix 52, from the bottom end 26 of receptacle 12 to a position beneath cap 14. The outlet end 38 of tube 34 conveys the solution into the top end of bubble trap 20.

Bubble trap 20 works in conventional manner to remove air bubbles from the solution. Specifically, as solution is deposited into bubble trap 20, any air in the solution rises to the top of the solution pool and escapes through air release port 56 located in the cap 22 of bubble trap 20. An outlet port 58 is located in the bottom end of bubble trap 20 and a elongated filter 60, such as a 120μ screen covers the outlet opening and extends within the bubble trap 20. Filter 60 functions in the conventional manner to aid in removing air from the solution and to remove any particulate matter that may have entered the system.

Finally, it should be noted that top to bottom and bottom to top flow of the solution through the double-coiled helix in combination with the smooth inner walls of the tube 34 facilitates the maintenance of a low percentage of air bubbles in the solution. The coiled flow path prevents splashing motion which would tend to generate gas bubbles that might be carried to the patient. Further, in contrast to other flow patterns, a coiled flow pattern in and of itself facilitates the separation of air from the blood.

While it is preferred that tube 34 be manufactured of stainless steel, other materials may be used such as PVC. Stainless steel is preferred because heat is transferred more rapidly through metal than it is through plastics. Therefore when coolant contacts tube 34 as will be discussed later, the hypothermic solution is more efficiently cooled using a metal coil.

In accordance with the invention there is provided means connected to the first chamber for supply coolant to the first chamber. As embodied herein, the coolant supplying means includes port 62 located in the bottom 26 of receptacle 12. Port 62 is an inlet for coolant, such as chilled water. Preferably, port 62 includes a tubular portion, such as a Hansen connector, extending from the bottom 26 of receptacle 12 for connection to the tubing of a coolant circuit (not shown).

In accordance with the invention there is also provided flow path means extending between the first and second chambers for permitting fluid flow between the first and second chambers, the flow path means including means for uniformly distributing coolant over the elongated tube means. As embodied herein, flow path means includes a space 65 between the upper edge 64 of partition 32 and the top 66 of cap 14. Due to the space 65, when first chamber 28 fills with coolant, it flows over the upper edge 64 of partition 32, and into second chamber 30. The upper most edge 64 of partition 32 serves as a flow ring for uniformly distributing coolant over the elongated tubing 34. Specifically, assuming heat exchange device 10 is maintained in a level position, as chamber 28 overflows with coolant, coolant will uniformly flow over the ring shaped upper edge 64 of partition 32 thereby uniformly covering coil 34.

Coolant flow occurs in an umbrella-like pattern as illustrated in FIG. 2. Specifically, coolant enters receptacle 12 at the bottom end 26, travels upward towards cap 14, and then overflows into the second chamber and travels downward back towards the bottom 26 of receptacle 12.

Preferably, the inner coil 54 of the double coiled helix is spaced from partition 32 so that coolant may flow on either side of the double coiled helix. Tubing 32 is held in a fixed position away from partition 32 by a series of bosses 55, 57, 59, and 61 that extend from cap 14.

The means for uniformly distributing coolant may also include cap 14 which is dome shaped in order to direct coolant over tube 34. If coolant is provided to receptacle 12 at a high rate through port 62, coolant may be urged against lid 14 creating a pressure within heat exchange device 10. The domed shaped of cap 14 further aids in distributing rapidly flowing coolant over tube 34 in an umbrella-like manner as illustrated in FIG. 2.

In accordance with the invention there is also provided means connected to the second chamber for evacuating coolant from the second chamber. As embodied herein, the evacuating means includes an outlet port 68 disposed in the bottom 26 of first chamber 28. Outlet port 68 is shaped in a manner similar to inlet port 62 for connection to the tubing of a coolant circuit (not shown). After coolant flows over tubing 34 it collects in the bottom 26 of receptacle 12 and is evacuated through outlet port 68.

The operation of the invention will now be described. After a priming stage has occurred, the heat exchange device illustrated in FIG. 1 is connected to an extracorporeal blood circuit. Specifically, the inlet end 36 of tube 34 is connected to receive blood from a patient under treatment, and the outlet port of bubble trap 20 is connected to tubing for returning blood to the patient under treatment. Under normal use blood flow is in the range of 50-500 ml/min. The circuit also includes an inlet for the introduction of anticoagulant such as potassium. Preferably, the anticoagulant inlet is located upstream of heat exchange device 10. If the potassium is added in crystalloid form, it may also be beneficial to employ a mixing device in the circuit to ensure uniform mixing of the potassium with the blood.

Coolant inlet port 62 is connected to a source of coolant, and coolant outlet port 68 is also connected to the coolant circuit for removing coolant from heat exchange device 10.

As a hypothermic solution of blood and potassium flows through double coiled helix 34, coolant in second chamber 28 overflows over the upper ring-like edge 64 of partition 32, uniformly covering tube 34 in an umbrella-like manner. In addition, a portion of the column of coolant in first chamber 28 is urged against the cap 14. The dome-like shape of the cap also distributes the coolant in an umbrella-like manner over the tube 34. Preferably, the coolant is circulated through the heat exchange device 10 at flow rates between 50 and 500 ml/min.

After the coolant flows over the tube 34 to bottom 26 of receptacle 12, it is evacuated from receptacle 12 via outlet 68. This flow of coolant over the tube 34 cools the hypothermic solution within tube 34 to a temperature capable of effecting cardioplegia in a patient under treatment. The hypothermic solution then enters bubble trap 20 through outlet end 38 of tube 34. Air is removed in bubble trap 20 and the cooled blood is returned to the patient along with the added potassium via outlet 58 in bubble trap 20.

The structure of the invention facilitates uniform cooling of the blood by eliminating pockets in which coolant would otherwise stagnate. With the present invention, coolant enters and exits heat exchange device 10 quickly and in an efficient manner so that the temperature within heat exchange device 10 is constant throughout the device. Because the entire volume of coolant in receptacle 12 is constantly replaced, it is possible to quickly change the temperature of the hypothermic solution by controlling the temperature and flow rate of the coolant flowing through the coolant circuit. Further the ring-like upper edge 64 of partition 32 ensures that all portions of tube 34 are constantly exposed to fresh coolant so that cooling is uniform throughout heat exchange device 10.

It will be apparent to those skilled in the art that various modifications and variations can be made to the present invention without departing from the scope and spirit of the invention. For example, the coiled tube 34 may be placed in the innermost chamber, and the umbrella-like flow can occur from the outermost chamber into the innermost chamber.

Other embodiments of the invention will be apparent to those skilled in the art from consideration of the specification and practice of the invention disclosed herein. Therefore, it is intended that the specification and examples be considered as exemplary only, with a true scope and spirit of the invention being indicated by the following claims.

What is claimed is:

1. A heat exchange device, comprising:
   a vessel having a top end and a bottom end, the vessel including a receptacle and a cap located on the receptacle, the cap being sealed to the receptacle and located on the top end of the vessel;
   a first chamber located in the vessel;
   a second chamber located in the vessel and being separated from the first chamber by a partition;
   elongated tube means located in the second chamber and being arranged in a convolution, the tube means for conveying a liquid to be cooled therein;
   means connected to the first chamber for supplying coolant to the first chamber;
   flow paths means extending between the first and second chambers for permitting fluid flow between the first and second chambers, the flow path means including means for uniformly distributing coolant over the elongated tube means; and
   means connected to the second chamber for evacuating coolant from the first chamber.

2. A heat exchange device as set forth in claim 1 wherein a bubble trap is connected to the vessel and wherein an outlet end of the tube means is connected to the bubble trap.

3. A heat exchange device as set forth in claim 1 wherein the first chamber is located in a central portion of the vessel and the second chamber is located about the first chamber.

4. A heat exchange device as set forth in claim 1 wherein the partition has a tubular shape.

5. A heat exchange device as set forth in claim 1 wherein the elongated tube means is a stainless steel tube.

6. A heat exchange device as set forth in claim 1 wherein the convolution is a double-coiled helix.

7. A heat exchange device as set forth in claim 1 wherein the liquid to be cooled is blood.

8. A heat exchange device as set forth in claim 1 wherein the supplying means is a port disposed in the first chamber.

9. A heat exchange device as set forth in claim 1 wherein the means for uniformly distributing coolant is an upper edge of the partition.

10. A heat exchange device as set forth in claim 9 wherein the means for uniformly distributing coolant also includes the cap, the cap having a domed shape.

11. A heat exchange device as set forth in claim 1 wherein the evacuating means is a port located in the second chamber.

12. A heat exchange device as set forth in claim 1 wherein the partition extends from the bottom end of the vessel to a position spaced from and beneath the cap.

13. A heat exchange device as set forth in claim 1 wherein the tube means includes an inlet end and an outlet end, the inlet and outlet ends of the tube means extending through openings located between the receptacle and the cap.

14. A heat exchange device, comprising:
 a vessel including a receptacle and a cap located on the receptacle, the cap being sealed to the receptacle and located on a top end of the vessel;
 a pair of concentric chambers located in the vessel, said pair of chambers including an innermost chamber and an outermost chamber separated by a partition.
 a coiled tube arranged in the outermost chamber for conveying a substance to be cooled;
 a port located in the innermost chamber for supplying coolant to the innermost chamber;
 means for directing coolant from the innermost chamber to the outermost chamber in an umbrella-like flow pattern; and
 a port located in the outermost chamber for evacuating coolant from the outermost chamber.

15. A heat exchange device as set forth in claim 14 wherein the coiled tube is arranged about the innermost chamber in a double helix configuration.

16. A heat exchange device, comprising:
 a vessel having a top end and a bottom end, the vessel including a receptacle and a cap located on the receptacle, the cap being sealed to the receptacle and located on the top end of the vessel;
 a first chamber located in the vessel;
 a second chamber located in the vessel and being separated from the first chamber by a partition;
 elongated tube means located in the second chamber and being arranged in a convolution, the tube means for conveying a liquid to be cooled therein;
 means connected to the first chamber for supplying coolant to the first chamber;
 flow path means extending between the first and second chambers for permitting fluid flow between the first and second chambers, the flow path means including means for uniformly distributing coolant over the elongated tube means;
 means connected to the second chamber for evacuating coolant from the second chamber; and
 a bubble trap connected to the vessel and having an inlet opening for receiving an outlet end of the tube means, the bubble trap also including an outlet opening.

17. A heat exchange device as set forth in claim 16 wherein the bubble trap is constructed of a transparent material.

18. A heat exchange device as set forth in claim 17 wherein the bubble trap is integrally formed with at least a portion of the vessel.

19. A method for cooling a liquid comprising the steps of:
 conveying coolant to a first open ended chamber having an outer wall;
 overflowing the first chamber with coolant;
 directing the overflowing coolant into a second chamber using a dome-shaped cap disposed above the first chamber, flowing the coolant uniformly over a coiled tube within the second chamber and surrounding the outer wall of first chamber;
 flowing a liquid to e cooled through the coiled tube; and
 evacuating coolant from the second chamber.

20. A heat exchange device comprising:
 a vessel including a receptacle with a cap located on the receptacle, the cap being sealed to the receptacle and located on a top end of the vessel;
 a first chamber located in the vessel;
 a second chamber located in the vessel and being separated from the first chamber by a partition;
 elongated tube means located in the second chamber and being arranged in a convolution, the tube means for conveying a liquid to be cooled therein;
 means connected to the first chamber for supplying coolant to the first chamber;
 flow path means extending between the first and second chambers for permitting fluid flow between the first and second chambers; and
 means connected to the second chamber for evacuating coolant from the first chamber.

* * * * *

UNITED STATES PATENT AND TRADEMARK OFFICE
CERTIFICATE OF CORRECTION

PATENT NO. : 5,269,749

DATED : December 14, 1993

INVENTOR(S) : Daniel C. KOTUROV

It is certified that error appears in the above-identified patent and that said Letters Patent is hereby corrected as shown below:

Claim 14, col. 7, lines 44-45, change "partition." to --partition;--.

Claim 19, col. 8, line 40, change "e" to --be--.

Signed and Sealed this

Twenty-sixth Day of April, 1994

Attest:

BRUCE LEHMAN

*Attesting Officer*    *Commissioner of Patents and Trademarks*